United States Patent

Cosentino

[11] Patent Number: 5,863,501
[45] Date of Patent: Jan. 26, 1999

[54] OXYGENATOR PRIMING METHOD

[75] Inventor: Louis C. Cosentino, Deephaven, Minn.

[73] Assignee: Minntech Corporation, Minneapolis, Minn.

[21] Appl. No.: 705,711

[22] Filed: Aug. 30, 1996

[51] Int. Cl.⁶ .................................................. A61M 1/18
[52] U.S. Cl. ............................... 422/48; 422/45; 422/46; 422/47; 210/177
[58] Field of Search ................................. 422/44, 45, 46, 422/48; 210/506, 193, 177; 252/321

[56] References Cited

U.S. PATENT DOCUMENTS

| 3,468,631 | 9/1969 | Raible et al. | 422/46 |
| 3,989,626 | 11/1976 | Bentley et al. | 210/177 |
| 5,162,102 | 11/1992 | Nogawa et al. | 422/48 |

FOREIGN PATENT DOCUMENTS

84/00015  1/1984  WIPO .

OTHER PUBLICATIONS

Kittle, C. Frederick, M.D., et al, Effect of a Nonionic Surface–Active Agent on Blood Viscosity and Platelet Adhesiveness, May 1969, pp. I–249–I252, Supplement I to Circulation, vols. XXXIX and XL, Official Journal of the American Heart Association, Circulation, USA.

Hornick, Philip and George, Andrew, Blood contact activation: pathophysological effects and therapeutic approaches, 1996, Perfusion, 11: pp. 3–19, London.

Courtney, Pat, H., CCP, et al, Gross Air Handling Characteristics of Membrane Oxygenators: An In Vitro Study, 1994, pp. 6–12, vol. 26, No. 1, The Journal of Extra–Corporeal Technology, USA.

Royston, D., Systemic inflammatory responses to surgery with cardiopulmonary bypass, 1996, Perfusion, 11: pp. 177–186, UK.

Bearss, Mark, G., The Puzzling Case of the Cryoprecipitates, AMSECT Today, pp. 21–25, 41 with Citation 90 of 209 from 1993–96, USA.

Raymond, Chris, PH. D., Copolymer, Undergoing Trials, Could Improve Fibrinolytics' Effectiveness, May 5, 1989, pp. 2475, 2475–2480, vol. 261, No. 17, The Journal of the American Medical Association, USA.

Medtronic, Compendium of Scientific Information, Medtronic/Carmeda BioActive Surface, pp. 1–25 with cover/back pages Apr. 1991.

Specialty Coating Systems, Parylene Conformal Coating Specifications and Properties, pp. 1–11 with attachment of Parylene, A Biostable Coating for Medical Applications pp. 1–2, 4, and 3 attachments Aug., 1994.

*Primary Examiner*—Robert J. Warden
*Assistant Examiner*—Alex Noguerola
*Attorney, Agent, or Firm*—Barbara A. Wrigley

[57] ABSTRACT

A method for improving priming of an integrated oxygenator and heat exchanger which includes pretreating the integrated hollow fiber oxygenator and heat exchanger device with a surfactant. Pretreating the device coats the interior surfaces of the integrated hollow fiber oxygenator and heat exchanger with the surfactant, which facilitates the removal of entrapped air. An integrated hollow fiber oxygenator and heat exchanger having a surfactant coating on the interior surfaces is provided which subsequently allows for more efficient priming with an aqueous priming media.

5 Claims, 2 Drawing Sheets

OXYGENATOR PRIMING METHOD

FIELD OF THE INVENTION

This invention relates to the field of hollow fiber membrane type oxygenators. In particular, it relates to an integrated hollow fiber oxygenator and a hollow tube heat exchanger including a surfactant coating which subsequently allows for rapid and efficient priming of the integrated oxygenator and heat exchanger within an extracorporeal circuit used during cardiosurgery. This invention also relates to a method of improving priming of an integrated oxygenator and heat exchanger by pretreating the integrated oxygenator and heat exchanger with a surfactant.

DESCRIPTION OF THE RELATED ART

From the first operation to repair a heart in 1891 until the early 1950s, heart surgeons were limited by the problem of trying to work on the heart while it was still beating. The heart's constant motion, and the presence of blood that obscured the surgeon's view, made repairing heart defects a surgical challenge. Surgeons had to work quickly and there was always a danger of disrupting blood circulation to vital organs. The solution to this problem came in the late 1950s with the development of the first oxygenators.

In nature, deoxygenated blood from the veins returns to the heart's right atrium. From the right atrium, blood is pumped to the right ventricle, then through the pulmonary artery to the lungs. The lung oxygenates the blood while removing carbon dioxide as it passes through the lung's alveolar capillary network. Oxygenated blood is then returned to the left atrium by way of the pulmonary veins. Blood is then pumped through the mitral valve into the left ventricle and pumped back into the body's circulatory system. Cells are replenished with oxygen and carbon dioxide is taken up by the blood as the blood passes through the body's capillary system. After this gaseous exchange is accomplished, the blood is returned to the heart and the cycle is repeated.

During cardiopulmonary by-pass (CPB) surgery for example, venous blood is taken from the patient's circulation by means of a canula placed in the vena cavae. The blood "bypasses" the heart and lungs and enters what is referred to as the "extracorporeal circuit" or literally a circuit "outside the body." Oxygenation of the patient's blood takes place in an oxygenator much in the same way as it does in the natural process. After the blood is oxygenated and temperature regulated, it is returned to the patient's arterial circulation through a cannula so that the patient's body may utilize the oxygenated blood.

The oxygenation of the patient's blood may be accomplished utilizing a variety of devices incorporating a semipermeable membrane. Recently, this membrane takes the form of an asymmetric microporous hollow fiber membrane. These membranes are polymeric capillary tubes having an outside diameter equal to about 1 mm or less and the walls function as the semipermeable membrane. Conventional art hollow fibers have typically included regenerated cellulose materials and modified polyacrylonitrile material. However, it is difficult to control the porosity and pore size of these fibers, and for some applications, composite membranes including an ultra-thin layer contiguous with a more porous substrate are needed to provide the necessary strength.

Hollow fiber membranes may also be prepared from hydrophobic polymers such as polysulfones and polyaromatic polyamide polymers. The hydrophobic nature of the polymer presents difficulties in using these membranes in aqueous systems and, therefore, hydrophilic polymers have been incorporated directly into the fibers. However, this may only improve the wettability of the hollow fibers, i.e., air removal during the priming procedure described below. When these fibers are utilized in compartmented devices, such as within an oxygenation compartment of an integrated oxygenator and heat exchanger, the wettability of the entire device interior may not be significantly improved.

Prime Volume

Prime volume is the volume of liquid that the surgeon pumps through the extracorporeal system to "prime" it. Typically, prior to the initiation of surgery the total internal volume of the extracorporeal circuit, which includes the integrated oxygenator and heat exchanger, cardioplegia line, ventricular vent line, etc., must be primed. Priming is done to flush out any extraneous gas from the extracorporeal circuit prior to the introduction of the blood. The larger the priming volume, the greater the amount of priming solution present in the circuit which mixes with the patient's blood. The mixing of the blood and priming solution causes hemodilution. Hemodilution is disadvantageous and undesirable because the relative concentration of red blood cells must be maintained during the operation in order to minimize adverse effects to the patient.

In order to reduce the deleterious effects of hemodilution donor blood may be used. However, the use of donor blood is undesirable because while it reduces the disadvantages associated with hemodilution, donor blood presents complications such as compatibility and the potential transmission of disease. Alternatively, one may use hemoconcentrators to counter the effects of hemodilution. However, such devices add an additional cost to the procedure thus increasing an already expensive operation.

Another disadvantage of large prime volumes is the amount of time expended by the perfusionist in priming the circuit, which in turn increases the start-up time for surgery while operating personnel stand-by. The great majority of commercially available oxygenators have large prime volumes. Typically, the prime volume of the total extracorporeal circuit ranges from two to two and a half liters. Of that volume, the prime liquid in some commercially available oxygenators ranges from 550 mL to 750 mL.

Priming Procedure

As stated above, prior to initiating the cardiosurgery procedure, the entire extracorporeal circuit must be primed with a hemocompatible fluid, such as sterile saline, so that all the air which may be trapped within the extracorporeal circuit is removed. This has been typically accomplished by forcing, usually using gravity forces only, or pumping the priming fluid through the extracorporeal circuit. This "pushes" the extraneous gas out of the circuit, including an integrated hollow fiber oxygenator and heat exchanger. A majority of priming procedures require vigorous "tapping" of the oxygenator to dislodge trapped air from within the device. Evaluation of air removal is often merely a visual examination of the device. However, entrapped air is not always visible from the outside of the device and any air which may remain within the circuit during the cardiosurgery procedure causes decreased performance during the operation.

For example, the patient's blood may not be sufficiently oxygenated as it passes through the oxygenator. In hollow fiber type oxygenators, the oxygen flows through the lumens of the hollow fibers while the blood flows on the exteriors. Blood is oxygenated because of the oxygen concentration gradient that exists between the oxygen gas present in the hollow fiber lumens and the blood surrounding the exterior of the fiber. High oxygen transfer rates are desirable to make as much oxygen available to the patient's system as possible. Air bubbles which may remain in the oxygenator, usually between the exterior surfaces of the hollow fibers, will direct blood flow around the air bubbles thereby decreasing the amount of hollow fiber surface area available for blood contact. This maldistribution of the blood flow may contribute to inefficient gas exchange due to localized regions of blood stagnation.

Another example of the consequence possible due to residual air in the extracorporeal circuit is the increased potential for high pressure drop within the hollow fiber oxygenator. Pressure drop is the pressure differential between the blood inlet and the blood outlet port and measures the force that literally pushes the blood through the blood pathway of the integrated oxygenator and heat exchanger. Any air remaining in the integrated hollow fiber oxygenator and heat exchanger may interact with blood components. It is theorized that such interaction may activate the compliment cascade or other thrombogenic factors which then causes the blood to coagulate or clot. These clots may adhere to the interior surfaces of the integrated hollow fiber oxygenator and heat exchanger, again, causing maldistribution of the blood flow through the device. High pressure drop, i.e. high oxygenator inlet pressure, has been associated with this "clotting" phenomenon. High pressure drop stress component parts and connections of the integrated oxygenator and heat exchanger. High pressure drop may necessitate the replacement of the integrated oxygenator and heat exchanger during surgery which increases both time and expense of the surgical procedure.

Accordingly, there is a need for an integrated hollow fiber oxygenator heat exchanger which allows for more efficient priming of the integrated hollow fiber oxygenator and heat exchanger to reduce the priming time and to more effectively remove entrapped air from the integrated hollow fiber oxygenator and heat exchanger included in an extracorporeal circuit.

It is an object of the present invention to provide a method of improving priming of an integrated oxygenator and heat exchanger.

It is a feature of the present invention to provide an integrated oxygenator and heat exchanger including a surfactant coating within the device.

It is an advantage of the present invention to facilitate the removal of substantially all the entrapped air within the integrated oxygenator and heat exchanger.

SUMMARY OF THE INVENTION

The present invention provides an integrated hollow fiber oxygenator and heat exchanger including a surfactant to solve the problems outlined above that have heretofore inhibited efficient air removal in the integrated hollow fiber oxygenator and heat exchanger.

The integrated oxygenator and heat exchanger in accordance with the present invention includes (a) an oxygenation compartment defining an interior oxygenation chamber, wherein a plurality of hollow fiber membranes are disposed within the oxygenation chamber, each hollow fiber having an outer asymmetric microporous wall defining a lumen; (b) a heat exchange compartment in fluid communication with said oxygenation compartment, the heat exchange compartment defining an interior heat exchange chamber, wherein a plurality of hollow heat exchange tubes are disposed within said heat exchange chamber; and (c) a surfactant coating within said oxygenation chamber and said heat exchange chamber.

Also in accordance with the present invention is a method for pretreating an integrated oxygenator and heat exchanger including providing an integrated oxygenator and heat exchanger including oxygenation compartment defining an interior oxygenation chamber and a heat exchange compartment in fluid communication with the oxygentation compartment, the heat exchange compartment defining an interior heat exchange chamber; and flushing the integrated oxygenator and heat exchanger with a surfactant, wherein the surfactant is in an amount sufficient to coat a substantial portion of the oxygenation chamber and the heat exchange chamber.

One advantage of the method of the present invention is to reduce the time required for pre-operative set up by reducing the priming time. Another advantage of the present invention is to decrease the potential for high pressure drop during the cardiosurgery procedure and, thus, reducing the likelihood of a device change out.

DESCRIPTION OF A PREFERRED EMBODIMENT OF THE PRESENT INVENTION

Figure 1:
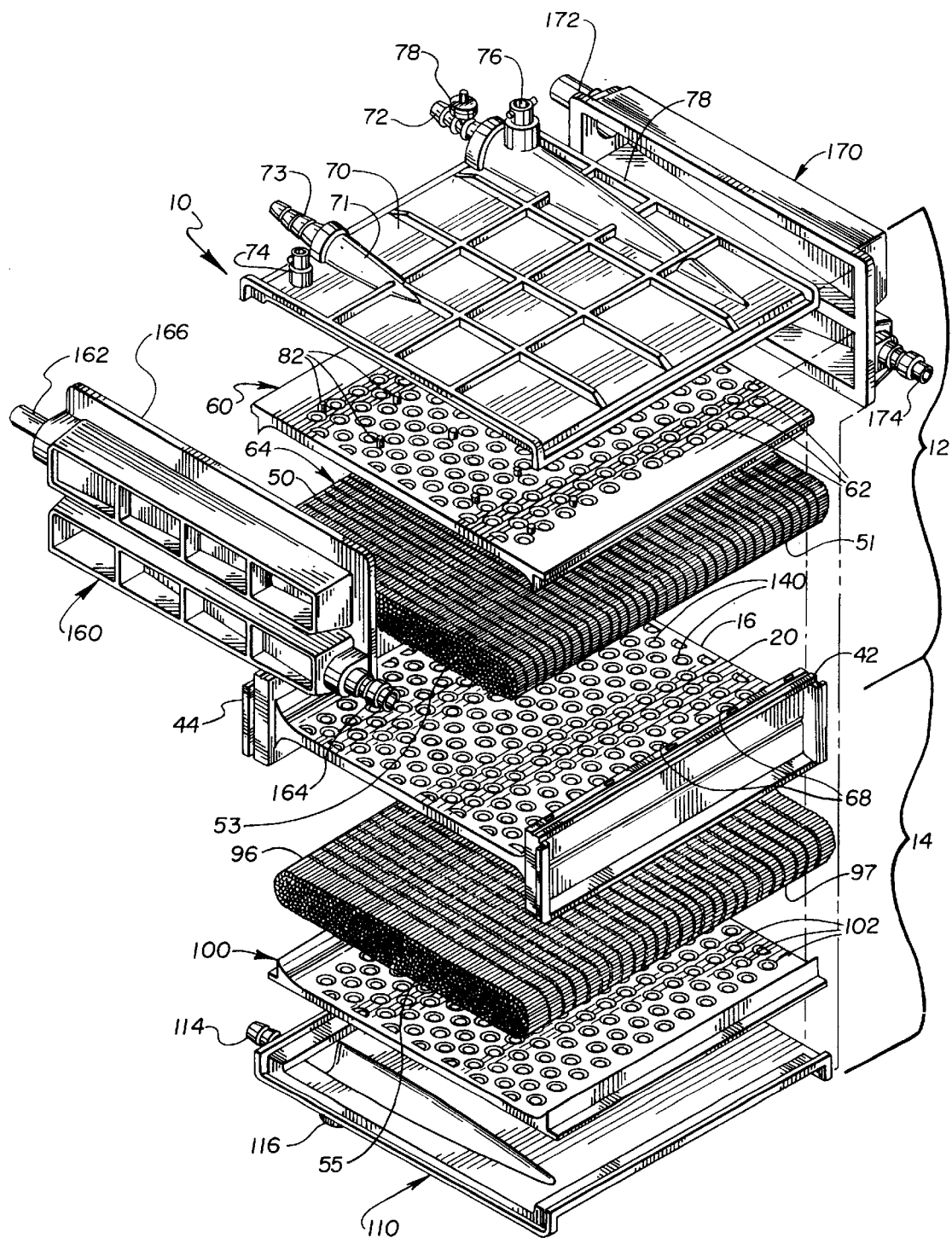
FIG. 1 is an exploded pictorial view of the integrated oxygenator heat exchanger which may be suitable for use in the present invention.
Figure 2:
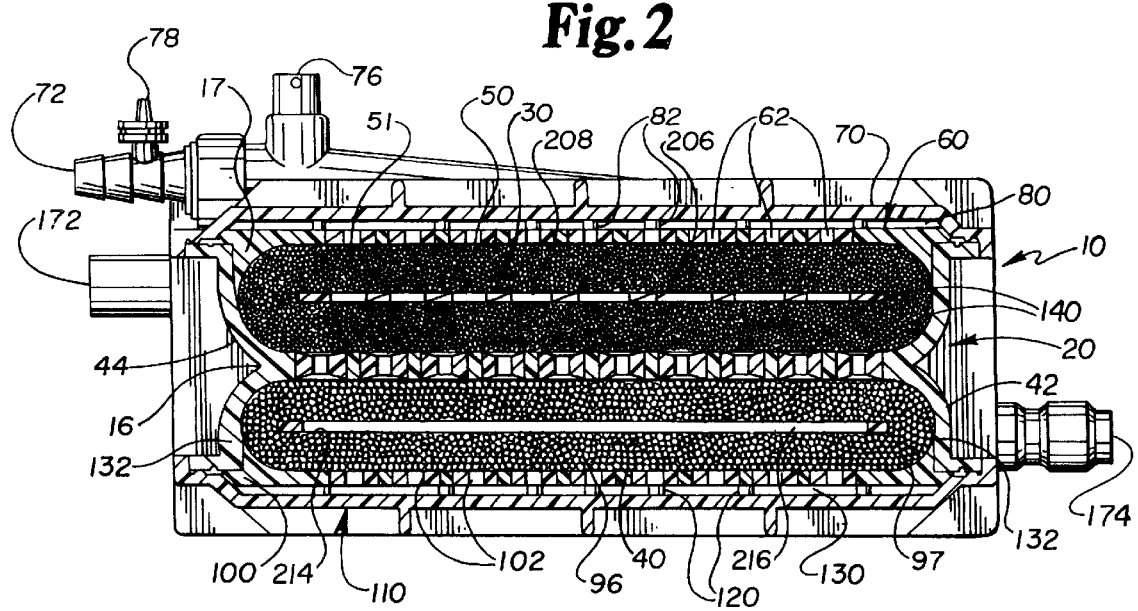
FIG. 2 is a cross sectional view of the integrated oxygenator heat exchanger.

FIGS. 1 and 2 depict an embodiment of an integrated oxygenator heat exchanger which includes an oxygenator 10 with a wound heat exchanger 14 suitable in accordance with the present invention. Device 10 generally includes housing 17. Housing 17 includes first and second diffuser plates 60,100 and a generally H-shaped in cross section core member 20 which includes a perforated center divider 16 and first and second opposing side walls 42,44 defining a first chamber 30 and second chamber 40. Each chamber 30,40 is a longitudinally extending groove contained within housing 17. Center divider 16 forms the bridge between the outside legs 42,44 of the "H" of core member 20. Gas exchange (oxygenation) compartment 12 includes first chamber 30 and heat exchange compartment 14 includes second chamber 40. Gas exchange compartment 12 and heat exchange compartment 14 are separated by a common center divider 16.

A. Gas Exchange Compartment

Gas exchange compartment 12 includes the area defined by first chamber 30. First chamber 30 is filled with hollow fibers 50 knitted together into a mat which is then wound into a generally cylindrical to elliptical shape. The wound bundle is shown at 51.

Each of the hollow fibers 50 is a membrane designed for gas exchange. Each hollow fiber may comprise a porous resin capable of gas transfer such as polypropylene, polyethylene or other biocompatible suitable material which provides a gas exchange. The fibers are liquid impermeable. Suitable fibers for this purpose are well known and commercially available from a number of vendors including Mitsubishi Rayon Co., Ltd. of Tokyo, Japan and Celanese Chemical Co. of New York, N.Y.

A diffuser plate 60 as shown in FIGS. 1 and 2 covers the upper ply of wound hollow fiber bundle 51 and is attached to legs 42,44 along its side edges. Diffuser plate 60 includes a plurality of chamfered orifices 62 which are spaced throughout the diffuser plate 60. Orifices 62 channel the passage of blood through plate 60 from first chamber 30. Plate 60 is constructed such that each orifice is chamfered to minimize sharp edges which might damage the hollow fibers.

The diffuser plate 60 bears against the wound hollow fiber membrane bundle 51 within first chamber 30. The plate 60 assists in holding the hollow fibers at the desired pack density of fibers per unit area within the first chamber 30 and is also assisted in that purpose by cover 70. The chamfered orifices in plate 60 allow blood to pass through wound bundle 51 from diffuser plate 20 in a substantially planar manner. This provides optimum exposure of the blood to fiber surfaces and minimizes the pressure drop across the unit. It also aids in eliminating potential areas of stagnation which decreases efficiency and might give rise to clotting.

The cross section of the hollow fiber membrane wound bundle so formed preferably has generally the form of a rectangle with rounded corners, a segment of a circle or semicircle with rounded edges, or an ellipse. These types of shapes produce space-saving configurations and prime volume-reducing wound hollow fiber membrane bundle. After the potting procedure is completed, the rectangular portion of the hollow fiber membrane wound bundle encompasses the functional area while the rounded edges are non-functional because the higher pack density on the sides causes substantial resistance to flow.

B. Heat Exchanger Compartment

The heat exchanger compartment 14 includes the region defined by second chamber 40. Chamber 40 includes hollow tube wound bundle 96 comprised of a plurality of hollow tubes 97 formed into a mat as seen in FIG. 1. The individual heat exchange hollow tubes 97 are preferably formed from a polyurethane resin such as B.F. Goodrich Estane™ 58091.

The heat exchange tubes of the present invention preferably have an outside diameter of from approximately about 0.025 inches (635 $\mu$m) to about 0.040 inches (1,016 $\mu$m) and most preferably have an outside diameter of 0.033 inches (840 $\mu$m). The tubes also preferably have a wall thickness of from approximately about 0.002 inches (50 $\mu$m) to 0.006 inches (152 $\mu$m) and most preferably have a wall thickness of about 0.004 inches (120 $\mu$m). The formation of heat exchanger tubes may also be from stainless steel.

In addition, while the efficiency of the heat exchanger is an important design consideration, it is vital that there is no leakage between the water path (heat exchange media) and blood path. If the design of the oxygenator does not provide for a leak-proof seal between the water and blood paths, hemolysis of red blood cells will result. The use of polyurethane heat exchange tubes (instead of stainless steel coils) and polyurethane end-potting compounds provides a leak-proof seal. The compatibility between the polyurethane tubes and the potting compound thereby greatly increases the effectiveness of the product vis a vis patient safety.

The cross section of the hollow tube heat exchanger wound bundle 96 so formed preferably has the form of a rectangle with rounded corners, a segment of a circle or semi-circle with rounded edges, or an ellipse. These types of shapes produce space-saving configurations and prime volume-reducing wound hollow tube bundles. After the potting procedure described below is completed, the rectangular portion of the hollow tube heat exchanger bundle encompasses the functional area while the rounded edges are non-functional because the higher pack density on the sides causes substantial resistance to flow.

As in the case of the oxygenator diffuser plate 60, the heat exchanger diffuser plate 100 is preferably separated from cover 110 by a plurality of nodes 120. Nodes 120 may be joined to cover 110 and diffuser 100 thereby defining blood distribution manifold 130 therebetween.

Diffuser plate 100 may be deleted. In that case, the hollow tube heat exchanger wound bundle is placed in second chamber 40 flush against a distributor blood plate means similar to blood plate 110 to control pack density. Distributor blood plate means (not shown) will have a pattern of V-shaped, X-shaped or diamond shaped grooves cut into the interior side touching the hollow tube heat exchanger wound bundle which serves the same purpose of blood distribution manifold 130, that is to create a path from which the blood can flow. Alternatively, distributor blood plate means can be constructed in a honeycomb pattern or with raised ribs on the interior side thereof, which ribs or honeycomb pattern will have a groove or channel cut into each one or distributor blood plate means may also be constructed with an outwardly extending depression in the surface thereof to create the blood distribution manifold. The elimination of diffuser plate 100 cuts down on production costs while maintaining the desired characteristics.

The integrated oxygenator and heat exchanger unit may then be end potted at each end with a polyurethane potting compound. Centrifugal end potting is well known in the art and is, for example, disclosed in U.S. Pat. No. 4,389,363 to Molthop.

Suitable potting compounds are available from Caschem, Inc. of Bayonne, N.J. A polyurethane casting system of Caschem, Inc. is described in U.S. Reissue Pat. No. 31,389. After potting, the hollow fibers and hollow tubes are reopened by conventional techniques such as by slicing through the potted bundle with a sharp knife to expose the interior of the fibers. The potting compound 185 provides a superior seal which provides maximum assurance that the seal will not leak.

The core 20 allows the potting of the heat exchange bundle 96 and the oxygenator bundle 51 to be performed simultaneously. The process of end potting tends to be time consuming and eliminating the need for two separate end potting procedures represents a marked improvement over commercially available units. Also, a single step potting reduces the possibility of leakage around the potted edges.

Referring to FIGS. 1 and 2, blood outlet port 72 and blood inlet port 114 preferably are constructed and arranged such that blood is directed across substantially the width of the fiber and tube bundles in the respective chambers.

Blood flows from the heat exchanger chamber 40 into the oxygenator chamber 30 by passing through perforations 140 in center divider 16. Center divider 16 is preferably constructed and arranged as described above for diffuser plate 60 and the same considerations apply as to the number and size of perforations 140.

After the hollow tube heat exchanger wound bundle 96 and hollow fiber membrane wound bundle 51 have been end potted and reopened, the device is completed by attaching first and second headers 160 and 170. Headers 160,170 provide gas and heat exchange media inlets and outlets to the open ends of the hollow fiber membrane wound bundle 51 and the hollow tube heat exchanger wound bundle 96.

Operation

In operation, blood entering inlet 114 sweeps through manifold 130 and uniformly contacts the heat exchanger bundle after passing through the diffuser 100. Manifold 130, in conjunction with diffuser 100 provides excellent blood flow distribution through the hollow tube heat exchanger wound bundle 96 where the blood is cooled and warmed by liquid entering heat exchange media inlet 174 and passing through the interior lumens of hollow tubes 97 and exiting through heat exchange media outlet 164.

The blood proceeds through the orifices 140 in core 20 and comes into contact with the hollow fiber membrane wound bundle 51 where it is oxygenated by gas entering the lumens of the individual hollow fiber membranes 50 from gas inlet 162 and exiting through gas outlet 172. Oxygenated blood then passes through orifices 62 in diffuser 60 and collects in blood collecting manifold 80. Blood then exits the oxygenator from blood outlet 72 where it is then circulated back to the patient.

Nonintegrated Units

If an oxygenator is not needed in an integrated unit, the oxygenator features may be utilized as a separate unit by providing a core having a U-shaped cross-section. Center divider 16 becomes a replacement for diffuser plate 100 and will be supported in a spaced relationship to the outer case. The blood plate would then be secured to the center divider. Of course, first and second headers would only need gas inlets and outlets. The oxygenator thus described provides all of the advantages found in the oxygenator compartment of the integrated device. It may be used in conjunction with systems having their own separate heat exchange units if desired.

The heat exchanger compartment described above for the device may be produced as a nonintegrated unit without an oxygenating compartment. A heat exchanger may be constructed by utilizing a core having a U-shaped cross-section such that center divider 16 is enclosed within blood plate 70. As above, the headers would be modified, in this case to provide heat exchanger media inlets and outlets.

Although the device is shown in the figures with a core having an H-shaped cross-section, the advantage of the invention may also be attained with a device in which the hollow tube heat exchanger wound bundle is generally perpendicular rather than parallel to the hollow fiber membrane wound bundle oxygenator fibers. Such a device may be made by moving the lower portions of legs 43,42 below the center divider to the other edges of the center divider. In such a construction the end caps would need to be separate and two separate end pottings would be required.

Pretreatment

The present invention provides a method for improving priming of an integrated oxygenator and heat exchanger including pretreating an integrated oxygenator and heat exchanger having an oxygenation compartment defining an oxygenation chamber and a heat exchange compartment defining a heat exchange chamber with a surfactant, wherein the surfactant is in an amount sufficient to coat a substantial portion of the oxygenation chamber and the heat exchange chamber. A method for pretreating an integrated oxygenator and heat exchanger includes (a) providing the integrated oxygenator and heat exchanger including an oxygenation compartment defining an interior oxygenation chamber and a heat exchange compartment in fluid communication with the oxygenation compartment, the heat exchange compartment defining an interior heat exchange chamber; and (b) flushing the integrated oxygenator and heat exchanger with a surfactant, wherein the surfactant is in an amount sufficient to coat a substantial portion of the oxygenation chamber and the heat exchange chamber. Once the integrated oxygenator and heat exchanger device is flushed, the surfactant is drained from the device and is dried. Of course, prior to use in a cardiosurgery procedure, the pretreated integrated oxygenator and heat exchanger is sterilized by any conventional method.

Pretreating the integrated oxygenator and heat exchanger device with a surfactant increases the wettability of the surfaces within the oxygenation chamber and the heat exchange chamber during the priming procedure with an aqueous media (described above) and the subsequent recirculation of a patient's blood during cardiosurgery. It is theorized that residual surfactant remains on the surfaces within the oxygenation chamber and the heat exchange chamber, even after sterilization, and this presence of the surfactant decreases the surface tension between the solid surfaces within the chambers and the liquid surface of the subsequent aqueous priming solution. The decrease in surface tension between the two surface types may facilitate the removal of substantially all the entrapped air within the device upon priming.

The surfactant may be amphoteric, zwitterionic, nonionic, anionic, cationic or a mixture thereof. A representative, non-limiting list of useful amphoteric surfactants includes lauroamphocarboxyglycinate, e.g., MIRANOL 2MHT MOD available from Miranol, Inc. (Dayton, N.J.) or synergistic constituents thereof. A representative, non-limiting list of useful zwitterionic surfactants includes B-N-alkylaminopropionic acids, N-alkyl-B-iminodipropionic acids, fatty acid imidazoline carboxylates, N-alkyl betaines, sulfobetaines, sultaines, and amino acids (e.g., asparagine, L-glutamine, etc.). A representative, non-limiting list of useful anionic surfactants include aromatic hydrophobic based acid esters and anionic fluorochemical surfactants. A representative, non-limiting list of cationic surfactants includes methyldbis-hydrogenated tallow amido-ethyl, 2-hydroxylethyl ammonium methyl sulfate, water soluble quaternized condensate polymers, and cocoalkyl bis (2-hydroxyethyl) methyl, ethoxylated chlorides. A representative, non-limiting list of useful nonionic surfactants include alkoxylated alkylamines, ethanol, isopropanol, methanol, glycerine, alkylpyrrolidones, linear alcohol alkoxylates, fluorinated alkyl esters including amine perfluoroalkyl sulfonate, N-alkylpyrrolidones, alkoxylated amines, and poly(methylvinylether/maleic anhydride) derivatives. Others include oligomeric or non-monomeric species containing a C12–18 aliphatic and/or aromatic hydrophobic moiety and a hydrophilic functionality within the same molecule. Yet another group of includes difunctional block copolymers with terminal secondary hydroxyl groups and difunctional block copolymers with terminating primary hydroxyl groups. These block copolymers typically include repeating blocks of poly(oxypropylene) or propylene oxide (POP) and poly(oxyethylene) or ethylene oxide (POE). It will be appreciated that the surfactant must be nontoxic to and biocompatible with a human circulatory system. Preferably, the surfactant is a nonionic surfactant. More preferably, the surfactant is selected from difunctional block copolymers with terminal secondary hydroxyl groups, difunctional block copolymers with terminating primary hydroxyl groups, fluorinated alkyl esters, or mixtures thereof. Most preferably, the surfactant is selected from polyoxypropylene-polyoxyethylene block copolymer, amine perfluoroalkyl sulfonate, or mixtures thereof.

WORKING EXAMPLES

Example 1

Integrated oxygenator and heat exchanger units described above were flushed with an aqueous solution of amine perfluoroalkyl sulfonate, FC-99 FLUORAD Brand Fluorochemical Surfactant (3M, St. Paul, Minn.), as follows:

Set A: 2 units flushed with 10.0 wt. % FC-99

Set B: 2 units flushed with 1.0 wt. % FC-99

Set C: 2 units flushed with 0.1 wt. % FC-99

These Sets were flushed with the corresponding surfactant solutions for about 2 minutes at room temperature and at a flow rate of about 400 ml/min. Each unit was drained and connected to an air supply. A continuous air flow was supplied to the units until dry, which in this instance was overnight. Drying was accomplished at room temperature.

Example 2

Integrated oxygenator and heat exchanger units described above were flushed with an aqueous solution of a polyoxypropylene-polyoxyethylene block copolymer, PLURONIC® F68 Prill (BASF, Parsippany, N.J.), as follows:

Set D: 2 units flushed with 0.07 wt. % F68

Set E: 4 units flushed with 0.1 wt. % F68

Set F: 4 units flushed with 1.0 wt. % F68

Set G: 8 units flushed with 10.0 wt. % F68

These Sets were flushed with the corresponding surfactant solution as described for Sets A–C. Drying was also accomplished as in Sets A–C.

Two pretreated units from each of Sets A–G were primed by conventional procedure, which included drawing an aqueous priming solution through the pretreated units contained in an extracorporeal circuit simulating that used during cardiopulmonary by-pass surgery. Visual inspection during and post priming indicated that substantially all of the entrapped air was removed from within the oxygenation chamber and the heat exchange chamber.

While a description of the preferred embodiment has been presented, it is contemplated that various changes, including those mentioned above, could be made without deviating from the spirit of the present invention. It is therefore desired that the present embodiment be considered in all respects as illustrative, not restrictive, and that reference be made to the appended claims rather than to the foregoing description to indicate the scope of the invention.

I claim:

1. An integrated oxygenator and heat exchanger comprising:
    (a) an oxygenation compartment defining an interior oxygenation chamber, wherein a plurality of hollow fiber membranes are disposed within said oxygenation chamber, each hollow fiber having an outer wall defining a lumen;
    (b) a heat exchange compartment in fluid communication with said oxygenation compartment, said heat exchange compartment defining an interior heat exchange chamber, wherein a plurality of hollow heat exchange tubes are disposed within said heat exchange chamber, each hollow tube having an outer wall defining a lumen; and
    c) an aqueous solution of amine perfluoroalkyl sulfonates surfactant substantially coating said oxygenation chamber, said outer wall of said plurality of hollow fiber membranes, said heat exchange chamber, and said outer wall of said plurality of hollow heat exchange tubes.

2. The integrated oxygenator and heat exchanger recited in claim 1 wherein said outer wall of said hollow fiber membrane comprises an asymmetric, microporous outer wall.

3. A method for pretreating an integrated oxygenator and heat exchanger comprising:
    (a) providing an integrated oxygenator and heat exchanger comprising an oxygenation compartment defining an interior oxygenation chamber including a plurality of hollow fiber membranes disposed therewithin, each hollow fiber having an outer wall defining a lumen and a heat exchange compartment in fluid communication with said oxygenation compartment, said heat exchange compartment defining an interior heat exchange chamber including a plurality of hollow heat exchange tubes disposed therewithin, each hollow heat exchange tube having a outer wall defining a lumen; and
    (b) flushing said integrated oxygenator and heat exchanger with an aqueous solution of a fluorochemical surfactant in an amount equal to about 10 wt. %,
wherein said fluorochemical surfactant coats a substantial portion of said oxygenation chamber, said outer wall of said plurality of hollow fiber membranes, said heat exchange chamber, and said outer wall of said plurality of hollow heat exchange tubes.

4. The method for pretreating an integrated oxygenator and heat exchanger recited in claim 3, wherein said fluorochemical surfactant comprises amine perfluoroalkyl sulfonates.

5. A method for improving the priming of an integrated oxygenator and heat exchanger comprising:
    (a) pretreating an integrated oxygenator and heat exchanger with a surfactant comprising a 10 wt. % aqueous solution of amine perfluoroalkyl sulfonates, said integrated oxygenator and heat exchanger including an oxygenation compartment defining an oxygenation chamber including a plurality of hollow fiber membranes disposed therewithin, each hollow fiber membrane having an outer wall defining a lumen, and a heat exchange compartment defining a heat exchange chamber including a plurality of hollow heat exchange tubes disposed therewithin, each hollow heat exchange tube having an outer wall defining a lumen.
wherein said oxygenation compartment and said heat exchange compartment are flushed with said surfactant in an amount sufficient to coat a substantial portion of said oxygenation chamber, said outer wall of said plurality of hollow fiber membranes, said heat exchange chamber and said outer wall of said plurality of hollow heat exchange tubes.

* * * * *